United States Patent [19]

Amplatz et al.

[11] Patent Number: 4,485,815
[45] Date of Patent: Dec. 4, 1984

[54] DEVICE AND METHOD FOR FLUOROSCOPE-MONITORED PERCUTANEOUS PUNCTURE TREATMENT

[76] Inventors: Kurt Amplatz, 10 Evergreen Rd., St. Paul, Minn. 55110; Frank Kotula, 4058 Nevada Ave. North, New Hope, Minn. 55427

[21] Appl. No.: 412,594

[22] Filed: Aug. 30, 1982

[51] Int. Cl.³ .............................................. A61B 17/34
[52] U.S. Cl. ................................................ 128/329 R
[58] Field of Search .............. 128/329 R, 320 A, 654, 128/656–658, 665, 763, 765, 303.18; 604/272–274, 240–243, 164–169, 117, 51, 20–21

[56] References Cited

U.S. PATENT DOCUMENTS

| | | | |
|---|---|---|---|
| 3,702,935 | 11/1972 | Corey et al. | 250/58 |
| 3,812,842 | 5/1974 | Rodriguez | 128/2 A |
| 4,005,527 | 2/1977 | Wilson et al. | 33/111 |
| 4,007,732 | 2/1977 | Kvale et al. | 128/2 B |
| 4,091,497 | 5/1978 | Bade | 16/110 R |
| 4,202,349 | 5/1980 | Jones | 128/689 |
| 4,244,370 | 1/1981 | Furlow et al. | 128/303 R |
| 4,280,508 | 7/1981 | Barrada | 128/736 |

OTHER PUBLICATIONS

"Radiolucent Handle for Percutaneous Puncture Order Continuous Fluoroscopic Monitoring" B. Rusnak et al., Radiology (USA), vol. 141, No. 2, Nov. 1981.

Primary Examiner—C. Fred Rosenbaum
Assistant Examiner—C. W. Shedd
Attorney, Agent, or Firm—Kinney & Lange

[57] ABSTRACT

A device for performing percutaneous puncture treatment of a patient includes an elongate radiolucent plastic handle with a central portion and two opposite elongated end portions. A hollow radiopaque needle has a hub at its proximal end which is releasably mounted in the central portion of the handle so that the needle is perpendicular to an axis through the end portions. The distal end of the needle has a puncturing tip. An internal fluid passage in the needle is open to the tip and the hub so that fluid may be drained from a patient's body through the passage when the needle is inserted in the patient's body. The needle and central portion of the handle are aligned under a field of view of a fluoroscope. The handle is held by the grips which are outside of the field of view of the fluoroscope. While the doctor continuously monitors progress of the needle on the fluoroscope, the puncturing tip is inserted through the skin and moved to an internal location for aspiration of fluid. Medical personnel are safely outside of the field of view of the fluoroscope during the entire process.

17 Claims, 9 Drawing Figures

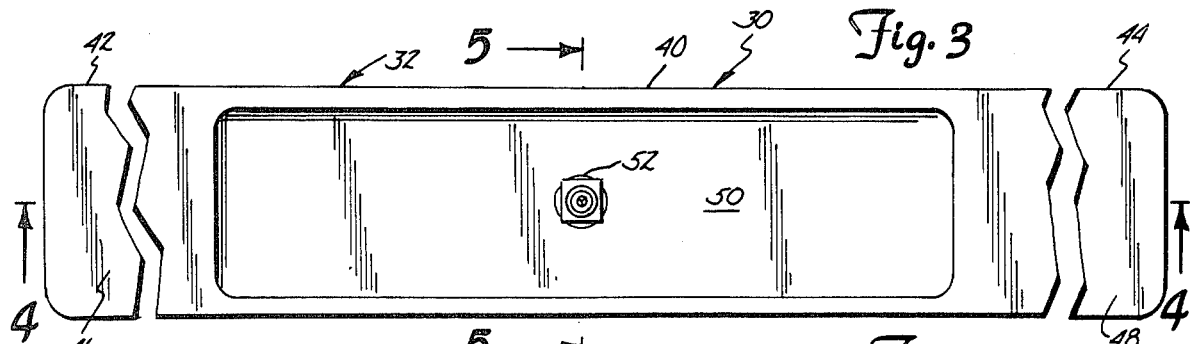
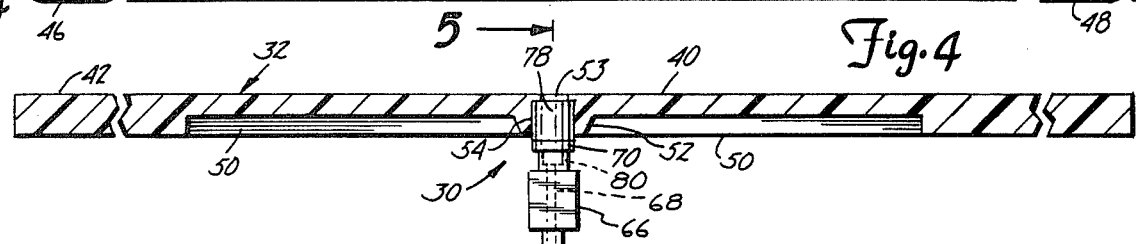
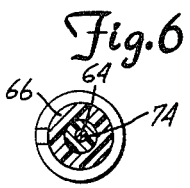
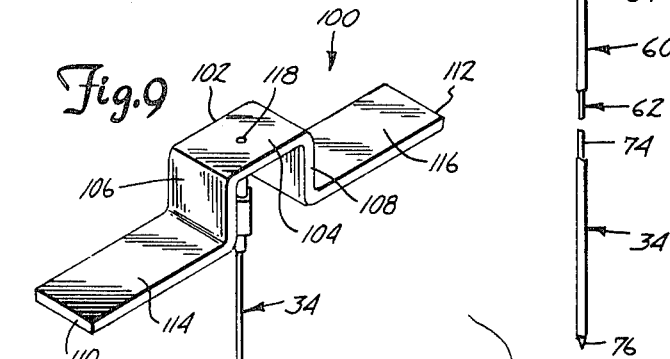
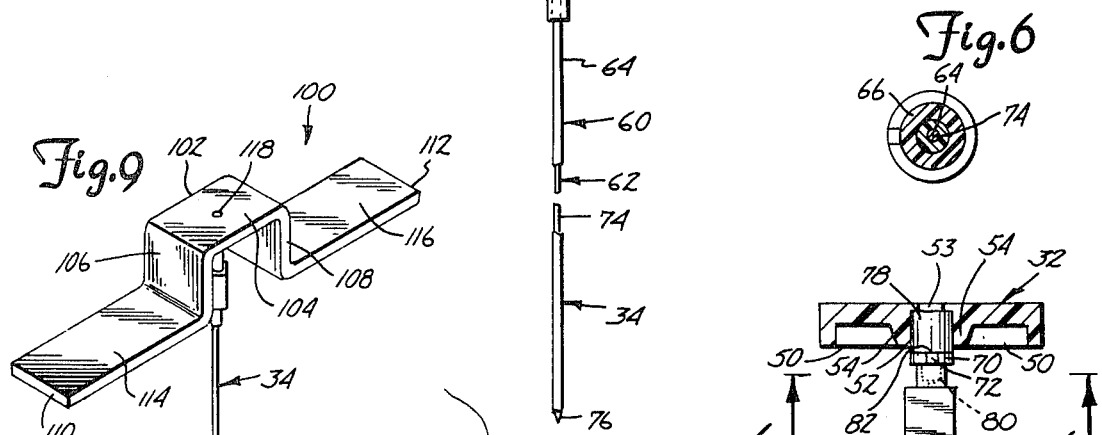
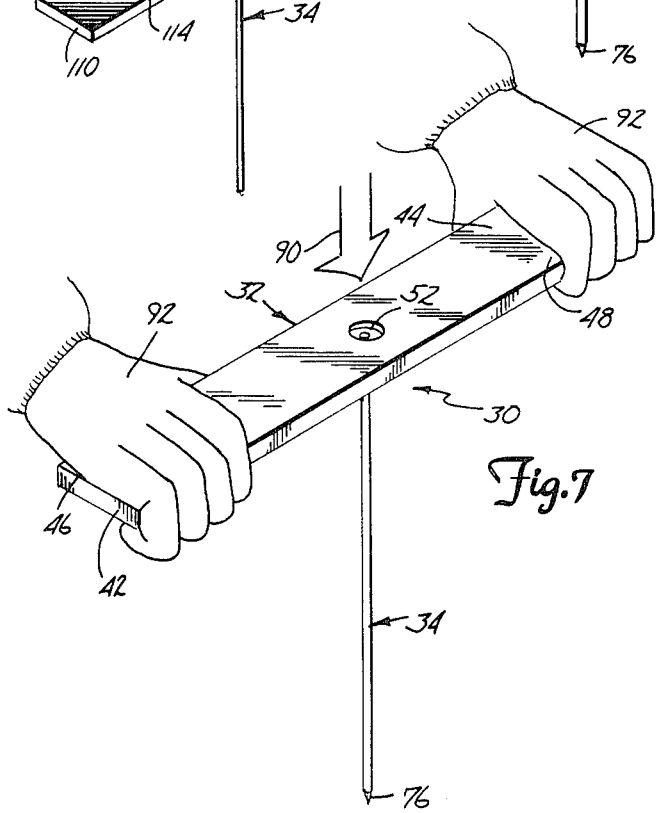
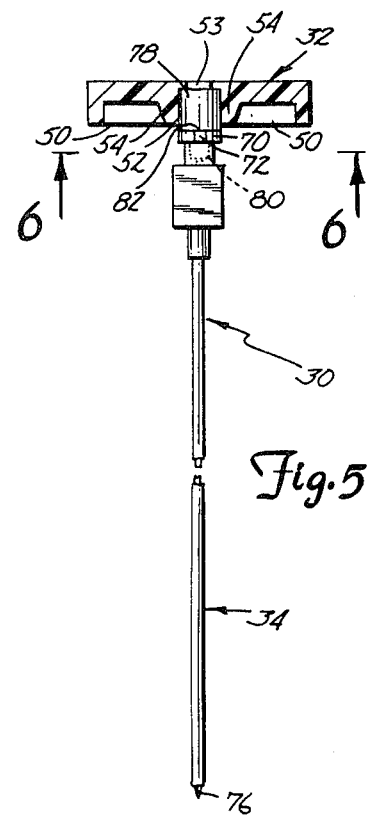

DEVICE AND METHOD FOR FLUOROSCOPE-MONITORED PERCUTANEOUS PUNCTURE TREATMENT

BACKGROUND OF THE INVENTION

1. Field of the Invention

This invention relates to devices and methods for percutaneous puncture treatment under fluoroscopic monitoring.

2. Description of the Prior Art

Percutaneous drainage is a technique for treating patients by puncturing the skin or cutaneous layer of the patient to drain fluid from an area inside the patient. For example, fluid can build up due to a plugged liver duct. A needle is inserted through the skin into the liver and the fluid is aspirated through a hollow passage in the needle.

In order to properly locate the needle, the patient is viewed with a fluoroscope during insertion of the needle. The organ to be punctured is usually treated with a dye which will cause the organ to appear on the fluoroscope. Because of the dangers associated with continual exposure to radiation from a fluoroscope, a doctor cannot handle the needle while the fluoroscope is activated. Therefore, the needle is usually held with a clamp during insertion. The needle is held a short distance from its puncturing tip with a long clamp, so that the doctor's hands are outside of the x-ray beam. The needle is then inserted through the skin or cutaneous layer. The needle is inserted perpendicular to a fluoroscopic field of view, so that the path of the needle can be followed on the fluoroscope monitor.

Because the needle is metallic, it is radiopaque and therefore visible on the fluoroscope monitor. The doctor can follow its path insertion and tell whether it is going straight. The fluoroscopic field of view is essentially perpendicular to the hollow passage in the needle, so that a straight insertion (i.e., parallel to the axis of the fluoroscope's x-ray beam) will result in a round view of the cross section of the needle. If the needle is oriented at an angle with respect to the axis of the x-ray beam, the doctor will see an elongated oval cross section rather than the round cross section.

Because of the difficulty in holding the needle with a long clamp, and because the needle typically used in the past has a bevelled tip which causes lateral deflection of the needle during insertion, in the prior art the needle can only be inserted a short distance at a time. The patient is instructed to hold his breath, and the needle is pushed in a short distance. The fluoroscope is then turned off so that the doctor can rotate the needle by 180° so that the orientation of the bevelled tip is reversed and can readjust the clamp another short distance up the needle. The fluoroscope is rotated to a horizontal position in order to determine whether the needle is still directed towards the proper area of the organ to be aspirated. Each time the patient breathes, the internal organ shifts slightly. It does not always return to the exact position it occupied prior to the breath. Therefore, for each small step of insertion the position of the organ relative to the needle must be checked in both the vertical and horizontal axes.

The incremental process repeats until the needle reaches the organ. In each step the patient suspends respiration, the doctor inserts the needle a short distance while viewing progress on the fluoroscope, the fluoroscope is turned off, the clamp is adjusted, the fluoroscope is rotated to check horizontal position, the fluoroscope is rotated back to the vertical, and the fluoroscope is reactivated to view the insertion of the needle. This laborious process involving many operations is required because of the difficulty in transmitting force to the needle from a distantly-held clamp without causing deflection of the needle from the desired path.

A patient search on the present invention uncovered the following United States patents:

| Inventor | U.S. Pat. No. | Issue Date |
|---|---|---|
| Thaxton | 2,737,957 | 03/13/56 |
| Carey et al | 3,702,935 | 11/14/72 |
| Rodriguez | 3,812,842 | 05/28/74 |
| Wilson et al | 4,005,527 | 02/01/77 |
| Kvavle et al | 4,007,732 | 02/15/77 |
| Bade | 4,091,497 | 05/30/78 |
| Jones | 4,202,349 | 05/13/80 |

U.S. Pat. No. 2,737,957 to Thaxton shows an elongated cross bar handle on a pipe cleaner.

U.S. Pat. No. 4,091,497 to Bade shows a tool handle constructed of plastic.

U.S. Pat. No. 3,702,935 to Carey et al discloses a mobile fluoroscopic unit which is used for positioning vascular catheters.

U.S. Pat. No. 3,182,842 to Rodriguez discloses an indexing scale which is mounted on the exterior of a patient's body. The scale has lead inlay lines and a movable lead inlay indicator. The lead parts are visible on the x-ray. The indicator is positioned to indicate the location of a vessel relative to the scale for catheterization.

U.S. Pat. No. 4,005,527 to Wilson et al. shows a depth gauge having alternating x-ray opaque and x-ray transparent sections of predetermined length. The depth gauge is inserted in a bone joint and viewed from the side with x-ray techniques to determine the distance into the joint which has been drilled.

U.S. Pat. No. 4,007,732 to Kvavle et al discloses a biopsy tool in which a wire with a barbed target is implanted in a breast. The target is held in place by the barbs. A wire extends from the target out through the cutaneous layer. A cutting tool with a central bore is then mounted over the wire and is guided by the wire in its cutting of tissue.

U.S. Pat. No. 4,202,349 to Jones discloses a radio-opaque blood vessel marker which is mounted on side wall portions of a blood vessel. Pulsation of the side walls of the vessel due to blood flow can be detected by fluoroscopic examination of the markers.

SUMMARY OF THE INVENTION

A device for performing fluoroscope-monitored percutaneous puncture treatment of a patient includes a handle having a radiolucent central portion and a grip portion extending away from the central portion. The grip portion includes a pair of grips on opposite sides of the central portion, so that the grips are outside of a fluoroscopic field of view when the central portion is positioned within the field of view. The handle is preferably made of a unitary bar of plastic.

A radiopaque hollow needle has a proximal end connected to the central portion of the handle and a distal end with a puncturing tip. An internal fluid passage in the hollow needle is open to both ends to permit draining of fluid from a patient's body through the passage while the needle is inserted in the patient's body.

The needle is preferably a diamond tip needle which has a hub at its proximal end for releasable connection to the central portion of the handle. The preferred needle includes a tube with the fluid passage and a shaft with the tip. The shaft is positioned in the passage in the tube during puncturing and is later withdrawn to allow aspiration.

The device is used in connection with a fluoroscope, which includes a radiation source for directing a penetrating radiation (e.g., x-ray) beam through a patient, a radiation receiver for receiving the beam, and a fluoroscopic monitor. The device is positioned between the receiver and a patient so that the needle is generally parallel to the beam. The device is held by the grips which are outside the beam (i.e., outside the fluoroscopic field of view), so that medical personnel are protected from exposure to the beam. The handle is urged toward the patient to puncture the cutaneous layer with the puncturing tip and to move the needle, preferably in one continuous motion, to a desired internal location. Movement of the needle is continuously monitored on the fluoroscope monitor. The medical personnel can view the needle generally in cross section. In a proper straight insertion, the needle appears symmetric. If the puncturing tip of the needle is deflected during its insertion so that the needle is at an angle to the beam axis, the needle appears oval or distorted.

BRIEF DESCRIPTION OF THE DRAWINGS

FIG. 3 is an enlarged bottom plan view of the device of FIG. 1.

FIG. 4 is a cross sectional view taken along line 4—4 of FIG. 3.

FIG. 5 is a cross sectional view taken along line 5—5 of FIG. 3.

FIG. 6 is a cross sectional view taken along line 6—6 of FIG. 5.

FIG. 7 is a reduced respective view of the device of FIG. 3 being gripped by a doctor.

FIG. 9 is a perspective view of a second embodiment of a device constructed according to the present invention shown in smaller scale than the first embodiment.

DETAILED DESCRIPTION OF THE PREFERRED EMBODIMENTS

Figure 1:
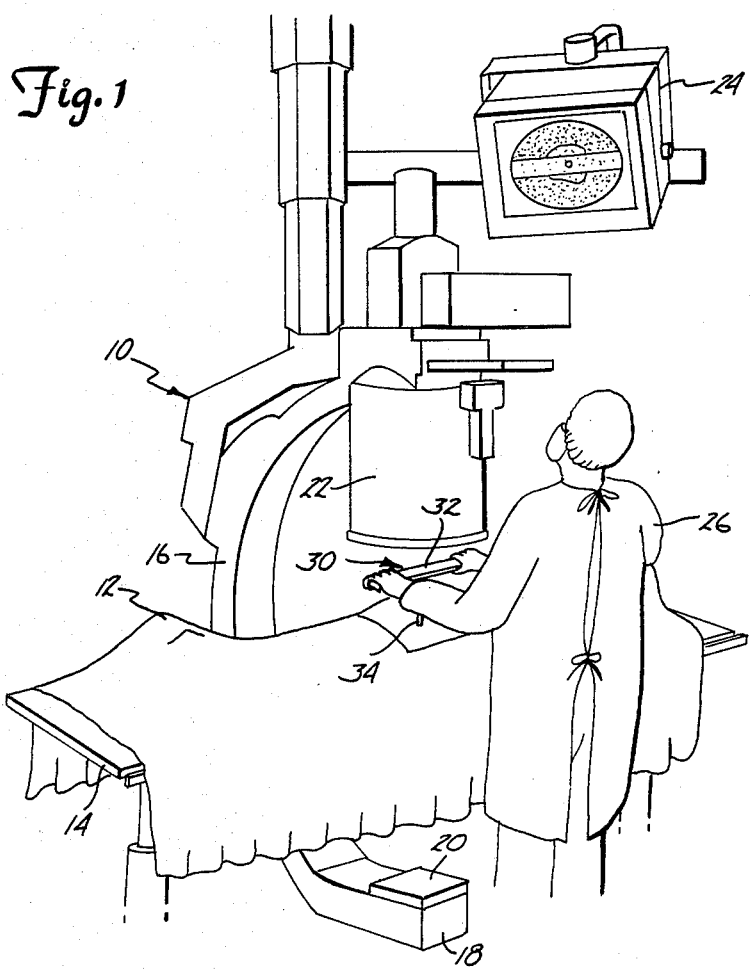
FIG. 1 is a perspective view of a doctor performing percutaneous puncture treatment on a patient using a device constructed according to the present invention, while viewing progress of the treatment on a fluoroscope monitor.

The percutaneous puncture treatment of the present invention is performed under monitoring by means for producing and viewing penetrating radiation such as fluoroscope 10 shown in FIG. 1. A patient 12 is laid on a table 14, which is essentially transparent to x-rays.

The fluoroscope 10 illustrated in FIG. 1 is of the type having a C-shaped arm 16. Table 14 and patient 12 are positioned within the C formed by arm 16. Fluoroscope 10 is, for example, an ARCOSKOP 110-3DM fluoroscope, and table 14 is a PTT-R table. Fluoroscope 10 has an x-ray tube unit 18 at a lower end of the C-shaped arm, which emits an x-ray beam in a generally upward vertical direction through a diaphragm 20. The x-ray beam is directed upward through the table 14 and an area of patient 12 to be viewed.

Figure 2:
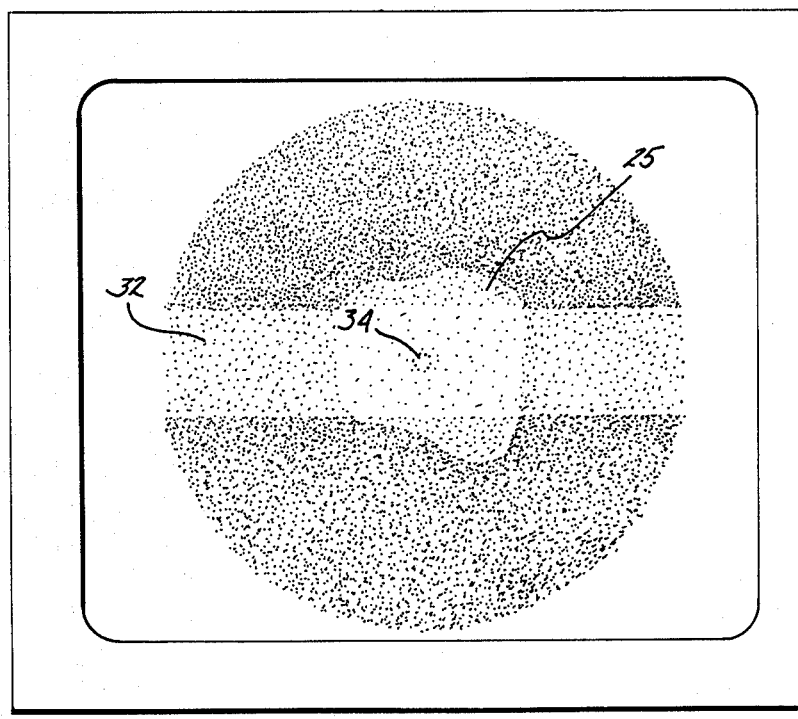
FIG. 2 is an enlarged plan view of the fluoroscope monitor of FIG. 1 showing representation of an internal organ of the patient and a needle being inserted.

The x-ray beam is received by an image intensifier 22, such as a SIRECON 2 Duplex Image Intensifier, which includes a television camera (not shown). A fluoroscopic field of view received by the camera in image intensifier 22 is projected on a television monitor 24. An example of such field of view is illustrated in FIG. 2.

Preparatory to percutaneous puncture treatment, an internal organ 25 of patient 12 is dyed so that it is radiopaque to x-rays. Patient 12 is aligned between tube unit 18 and image intensifier 22 so that the internal organ 25 is visible on television monitor 24.

A doctor 26 performs the puncture treatment utilizing a puncture device 30 which, in this example, has an elongate plastic handle 32 and a hollow needle 34. The doctor positions needle 34 against the skin of patient 12, with needle 34 generally parallel to the central axis of the x-ray beam which is directed upward from x-ray tube unit 18 to image intensifier 22. The fluoroscopic field of view is narrowed and needle 34 is positioned in the center of the field of view to minimize parallax.

While holding handle 32, doctor 26 remains outside of the path of the x-ray beam, as shown in FIG. 1. The doctor 26 asks patient 12 to suspend respiration. This assures that the organ 25 to be aspirated will not shift during insertion of needle 34. Doctor 26 then views needle 34 on television monitor 24 while pushing down on handle 32 to puncture the skin of the patient 12 and push needle 34 to its desired location in one continuous motion. Once needle 34 is in organ 25, fluoroscope 10 is turned off, and handle 32 is removed. Fluid can then be aspirated through hollow needle 34.

Organ 25 can be as small as 0.4 inches (one centimeter) in diameter or can be quite large, such as 14 inches (35 centimeters) in diameter. In the example illustrated organ 25 is approximately 1.2 inches (3 centimeters) in diameter. In FIG. 2, handle 32 barely shows against the dark background, since it is generally radiolucent. Handle 32 is preferably made of plastic. Needle 34, since it is metallic, is radiopaque and shows as white, against the darker background.

Doctor 26 determines if needle 34 is deflected during its insertion towards organ 36 by viewing the cross section of needle 34, as in FIG. 2. It should appear generally round, as shown. If the cross section of needle 34 appears oval or otherwise distorted on television monitor 24, it indicates that the direction of needle 34 is deflected from vertical (i.e., parallel to the axis of the x-ray beam) and must be corrected.

Because the doctor 26 can push downward on handle 32 with one generally continuous movement while viewing the progress of needle 34 on television monitor 24, the prior art problems of pushing the needle in small increments are avoided. By using handle 32, the insertion of needle 34 is accomplished during a single suspension of respiration by patient 12. The stable force-transmitting handle 32 allows insertion of needle 34 in a continuous movement. The doctor 26 need not worry about organ 25 shifting to a different position during successive breaths by patient 12.

With the system shown in FIG. 1, the doctor 26 also can check the depth of needle 34 after the insertion step. This is achieved by rotation of C arm 16 through 90°, so that x-ray tube 18 is on one side of patient 12, image intensifier 22 is on the opposite side, and the x-ray beam is directed horizontally through the patient 12. Small upward or downward movement of needle 34 can then be performed to obtain precise vertical positioning of the tip of needle 34 in organ 25.

A first embodiment of device 30 is shown in FIGS. 2-7. In this embodiment, handle 32 is a radiolucent elongate bar, preferably made of plastic. Handle 32 has a central portion 40 and a grip portion, which in this embodiment is a pair of end portions 42 and 44. End portions 42 and 44 extend away from central portion 40 in opposite directions. End portions 42 and 44 have hand grips 46 and 48, respectively.

Central portion 40 has a recess 50 in its bottom side. Recess 50 reduces the thickness of central portion 40, thereby making it more radiolucent. In this example, recess 50 is formed by routing a rectangle approximately one-half of the way through central portion 40. The illustrated handle 32 is approximately 10 inches (25 centimeters) long by one and one-half inches (3.8 centimeters) wide by one-quarter inch (0.6 centimeters) thick. Recess 50 is approximately five inches (12.7 centimeters) long by approximately one and one-quarter inches (3.2 centimeters) wide, and is about one-eighth inch (0.3 centimeters) deep.

Central portion 40 includes a needle receptacle 52. In this embodiment needle receptacle 52 is formed by cutting a bore 53 through central portion 40 along an axis perpendicular to a longitudinal axis of the elongate handle 32. Receptacle 52 extends into the hollow of recess 50 and, in this example, has tapered wall 54 which is formed in the routing process.

The needle 34 illustrated is a six-inch (15.2 centimeters), 18 gauge disposable needle, which contins two discrete parts; a hollow drain tube portion 60 and a puncturing shaft portion 62. Drain tube portion 60 includes a hollow metal tube 64 with its proximal end mounted in a hollow plastic fitting 66. Fitting 66 has a bore 68 therethrough and a top flange 70 containing an alignment slot 72.

Figure 8:
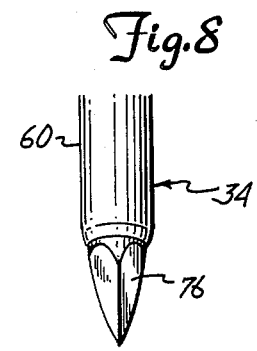
FIG. 8 is an enlarged framentary perspective view of a puncturing tip of the device of FIGS. 3–7.

Shaft portion 62 includes a metal puncturing shaft 74 which has a diamond puncturing tip 76, best illustrated in FIG. 8. Tip 76 is preferably a three-sided symmetric puncturing tip 76, which aligns a puncture along a central longitudinal axis of shaft 74. This style tip 76 avoids the problems of beveled-tip needles which tended to deflect laterally in the direction of the bevel. Shaft portion 62 inciudes a hub 78 which is mounted on the proximal end of shaft 74. Hub 78 has a plug 80, shown in dotted lines in FIGS. 4 and 5, with an alignment lug 82.

Shaft 74 is inserted through bore 68 and hollow tube 64 of drain tube portion 60 until plug 80 is inserted in the upper end of bore 60 of fitting 66, as illustrated. Lug 82 fits into alignment slot 72 in top flange 70. This assures a correct alignment of hub 78 and fitting 66, and prevents rotation of drain tube portion 60 relative to the shaft portion 62.

Hub 78 is at least partly generally cylindrical and is shaped and sized to fit snugly in needle receptacle 52, as shown in FIGS. 5 and 6. Bore 53 of needle receptacle 52 is preferably slightly reverse tapered to firmly hold hub 78 and to prevent hub 78 from extending through handle 32. When needle 34 is mounted in receptacle 52, a longitudinal axis of needle 34 is generally perpendicular to the longitudinal axis through handle 32. Puncturing tip 76 projects past the end of tube 64, so it is positioned to puncture the skin of patient 12.

Arrow 90 in FIG. 7 indicates the direction of the motion of handle 32 and needle 34 during insertion of needle 34 into the patient 12. This is the opposite direction of the upwardly projected x-ray beam from x-ray tube unit 18.

In FIG. 7, hands 92 of doctor 26 are shown holding grips 46 and 48 of end portions 42 and 44, respectively. When gripping handle 32 in the manner shown in FIG. 7, the doctor is able to transmit force downward along the longitudinal axis of needle 34. Receptacle 52 firmly holds needle 34 in a position perpendicular to handle 32, as described above, so that the force exerted by hands 92 of doctor 26 can be transmitted to puncturing tip 76.

Hands 92 are safely outside the fluoroscopic x-ray beam. This insures that doctor 26 is not exposed to radiation which could have dangerous cumulative effects during the many radiological treatments performed by the doctor.

Once needle 34 is inserted to its desired position in organ 25, handle 32 is moved upward and away from patient 12. Hub 78 remains in receptacle 52 as handle 32 is withdrawn. Shaft portion 62 is thereby withdrawn from drain tube portion 60. The passage of drain tube passage 60 is then open for aspiration of fluid.

A second embodiment of a handle 100 constructed according to the present invention is illustrated in FIG. 9. In this embodiment, central portion 102 of handle 100 is shaped like an inverted U, having a base 104 and legs 106 and 108. A grip portion includes end portions 110 and 112 which are integral with legs 106 and 108, respectively. End portions 110 and 112 extend away from central portion 102 on opposite sides, generally perpendicular to legs 106 and 108. End portions 110 and 112 have hand grips 114 and 116, respectively.

Central portion 102 has a receptacle 118 in its base 104 for receiving needle 34. Receptacle 118 is similar to receptacle 52 shown in the other figures.

The handle 100 of this second embodiment is also preferably made from a unitary piece of radiolucent plastic.

Handles constructed according to the present invention greatly simplify and speed the percuntaneous puncture treatment. Whereas previous puncture treatment has involved slow steps of insertion, the handle of the present invention allows continuous, one-step insertion during continuous fluoroscope monitoring. The continuous insertion by pressure of two hands on a handle constructed according to the present invention requires less dexterity than prior art methods. The two-hand grip provides a stable position for transmitting force to needle 34. This allows insertion to be accomplished quickly and more accurately. The hands of the medical personnel are always safely out of the x-ray beam even while transmitting pressure to the handle.

Although the present invention has been described with reference to preferred embodiments, workers skilled in the art will recognize that changes may be made in form and detail without departing from the spirit and scope of the invention.

What is claimed is:

1. A device for performing fluoroscope-monitored percutaneous puncture treatment of a patient in which an x-ray beam is projected from an x-ray source along a path defined by an x-ray beam axis through the patient to an x-ray receiver and in which a fluroscopic field of view is displayed based upon the x-ray beam received by the receiver, the device comprising:

a radiopaque needle for insertion into the patient's body, the needle having a distal end with a puncturing tip and a proximal end;

a handle having a radiolucent central portion and a grip portion extending away from the central portion, the grip portion having a pair of grips on opposite sides of the central portion so that the grips are outside of the x-ray beam when the central portion is positioned within the x-ray beam; and means for connecting the proximal end of the needle to the central portion of the handle so that the needle is generally perpendicular to an elongated axis through the grips, the needle being visible in the fluoroscopic field of view and the central portion of the handle appearing essentially transparent.

2. The device of claim 1 wherein the grip portion includes first and second end portions extending in opposite directions from the central portion.

3. The device of claim 2 wherein an elongated bar comprises the central portion and the first and second end portions.

4. The device of claim 1 wherein the central portion of the handle is made of plastic.

5. The device of claim 1 wherein the needle comprises:

a puncture shaft having the puncturing tip at its distal end and having its proximal end connected to the handle by the means for connecting; and a hollow drain tube coaxially aligned with and slidably mounted on the shaft for simultaneous insertion with the shaft into the patient, the drain tube being shorter than the puncture shaft, so that the puncturing tip of the shaft projects past a distal end of the tube for puncturing a cutaneous layer of the patient, and so that the shaft is adapted to be withdrawn from the patient without removing the tube to allow the draining of fluid from the patient's body through the tube.

6. The device of claim 1 wherein:

the needle has a hub on its proximal end; and the central portion has a receptacle for receiving the hub in a releasable connection.

7. A device for performing fluoroscope-monitored percutaneous puncture treatment of a patient in which an x-ray beam is projected from an x-ray source along a path defined by an x-ray beam axis through the patient to an x-ray receiver and in which a fluoroscopic field of view is displayed based upon the x-ray beam received by the receiver, the device comprising:

a radiopaque needle for insertion in a patient's body having a puncturing tip at its distal end and a hub at its proximal end; and an elongated handle having a radiolucent central portion and first and second end portions, the central portion receiving the hub of the needle and holding the needle generally perpendicular to a longitudinal axis through the elongated handle, and the end portions extending away from the center portion to first and second grips lying outside the x-ray beam when the central portion and the needle are positioned within the x-ray beam; the handle being adapted to permit application of force in a direction parallel to the needle to cause the needle to be inserted into the patient without exposing hands of medical personnal to the x-ray beam, while permitting continuous fluoroscopic monitoring of the needle and the patient during insertion.

8. The device of claim 7 wherein the central portion of the handle is made of a plastic material.

9. The device of claim 7 wherein the needle comprises:

a puncture shaft having the puncturing tip at its distal end and having the hub at its proximal end; and a hollow drain tube, coaxially aligned with and slidably mounted on the shaft for simultaneous insertion with the shaft into the patient, the drain tube being shorter than the puncture shaft so that the puncturing tip projects past a distal end of the tube for puncturing a cutaneous layer of the patient, and so that the shaft is adapted to be withdrawn from the patient without removing the tube to allow the draining of fluid from the patient's body through the tube.

10. A system for performing percutaneous puncture treatment of a patient, the device comprising:

means for directing a beam of penetrating electromagnetic radiation along a path defined by a beam axis through a patient;

viewing means for receiving the beam after it has passed through the patient and providing a real-time visible image of objects opaque to the beam which are within the path of the beam;

a handle having a central portion made of material essentially transparent to the beam, and a grip portion attached to and extending away from the central portion having a pair of grips on opposite sides of the central portion;

a needle, opaque to the beam, having a distal end with a puncturing tip and a proximal end connected to the central portion of the handle so that a longitudinal axis of the needle is generally perpendicular to an axis defined by the grips, the handle being adapted to insert the tip of the needle parallel to the beam axis through the cutaneous layer under continuous monitoring with the viewing means, the central portion being within the beam, while operator contact is with the grip portion outside of the beam, so that the needle is viewed in end view on the viewing means, whereby deflection of the needle from a direction parallel to the beam axis is indicated by change in appearance of the needle.

11. The system of claim 10 wherein the viewing means is a fluoroscope and the handle is radiolucent.

12. The system of claim 10 wherein:

the grip portion includes first and second elongated end portions extending in opposite directions from the central portion.

13. The device of claim 10 wherein the needle comprises:

a puncture shaft having the puncturing tip at its distal end and having its proximal end connected to the central portion of the handle; and a hollow drain tube coaxially aligned with and slidably mounted on the shaft for simultaneous insertion with the shaft into the patient, the drain tube being shorter than the puncture shaft so that the puncturing tip projects past a distal end of the tube for puncturing a cutaneous layer of the patient, and so that the shaft is adapted to be withdrawn from the patient without removing the tue to allow the draining of fluid from the patient's body through the tube.

14. A method of percutaneous puncture treatment of an internal organ of a patient, comprising the following steps:

treating the patient to cause a portion of an internal organ to be visible under fluoroscopic examination;

aligning a fluoroscope in relation to a patient's body for viewing the portion of the internal organ of the patient, the fluoroscope including an x-ray source for projecting an x-ray beam along a path defined by a beam axis through the patient to an x-ray receiver, and a display for displaying a fluoroscopic image based upon the x-ray beam received;

providing a needle with a puncturing tip at its distal end and a hub at its proximal end, the hub being connected to a radiolucent central portion of a handle, the handle having a grip portion extending away from the central portion with two grips on opposite sides of the central portion;

aligning the needle between the flouroscope and the patient with the needle positioned generally parallel to the beam axis, with the central portion of the handle aligned in the x-ray beam, and with the grip portions out of the x-ray beam;

gripping the handle by the grips;

activating the fluoroscope to view through the central portion, along the needle, and through the body of the patient;

moving the handle and needle toward the patient to puncture the cutaneous layer with the tip and moving the needle into the patient until the tip reaches a desired internal location in the organ; and continuously monitoring the progress of the needle on the fluoroscope by viewing an end view of the needle and watching for distortions in the appearance of the end view that indicate lateral deflection of the needle.

15. The method of claim 14 further comprising the step:

causing suspension of respiration of the patient during insertion of the needle.

16. The method of claim 15 wherein the needle is moved to its location during a single suspension of respiration.

17. The method of claim 14 wherein the needle comprises a puncture shaft extending from the hub to the puncturing tip, and a drain tube which is coaxially mounted on the shaft for simultaneous insertion with the shaft into the patient, the drain tube being shorter than the shaft so that the tip is exposed; and further comprising the step of:

moving the handle away from the patient along a path parallel to the axis of the needle after insertion, so that the shaft is withdrawn from the patient while the tube remains inserted in the patient to allow aspiration of fluid through the tube.

* * * * *